(12) United States Patent (10) Patent No.: US 9,119,942 B1
Rollins et al. (45) Date of Patent: Sep. 1, 2015

(54) GUIDEWIRE MANIPULATION DEVICE (71) Applicant: VESATEK, LLC, Irvine, CA (US)

(72) Inventors: Aaron Rollins, Miami Beach, FL (US); Tor Alden, Basking Ridge, NJ (US)

(73) Assignee: VESATEK, LLC, Irvine, CA (US)

( * ) Notice: Subject to any disclaimer, the term of this patent is extended or adjusted under 35 U.S.C. 154(b) by 0 days.

(21) Appl. No.: 14/704,879

(22) Filed: May 5, 2015

Related U.S. Application Data (63) Continuation of application No. 11/874,836, filed on Oct. 18, 2007, now Pat. No. 9,050,438.

(60) Provisional application No. 60/853,731, filed on Oct. 21, 2006.

(51) Int. Cl.
*A61B 5/00* (2006.01)
*A61M 25/00* (2006.01)
*A61M 25/09* (2006.01)

(52) U.S. Cl.
CPC .......... *A61M 25/09041* (2013.01); *A61M 2025/09116* (2013.01); *A61M 2025/09125* (2013.01)

(58) Field of Classification Search
CPC ............................................ A61M 25/09041
USPC .......................................................... 600/585
See application file for complete search history.

(56) References Cited

U.S. PATENT DOCUMENTS

| 3,748,435 A | 7/1973 | Reynolds |
|---|---|---|
| 3,847,140 A | 11/1974 | Ayella |
| 5,055,109 A | 10/1991 | Gould et al. |
| 5,243,997 A | 9/1993 | Uflacker et al. |
| 5,392,778 A | 2/1995 | Horzewski |
| 5,443,078 A | 8/1995 | Uflacker |
| 5,524,180 A | 6/1996 | Wang et al. |
| 5,524,635 A | 6/1996 | Uflacker et al. |
| 5,634,475 A | 6/1997 | Wolvek |
| 5,709,661 A | 1/1998 | Van Egmond et al. |
| 5,735,535 A | 4/1998 | McCombs et al. |
| 5,893,857 A | 4/1999 | Shturman et al. |
| 5,908,395 A | 6/1999 | Stalker et al. |
| 5,911,722 A | 6/1999 | Adler et al. |
| 6,027,460 A | 2/2000 | Shturman |
| 6,165,188 A | 12/2000 | Saadat et al. |
| 6,183,432 B1 | 2/2001 | Milo |
| 6,348,040 B1 | 2/2002 | Stalker et al. |
| 6,533,772 B1 | 3/2003 | Sherts et al. |
| 6,726,675 B1 | 4/2004 | Beyar |
| 6,752,800 B1 | 6/2004 | Winston et al. |
| 7,615,042 B2 | 11/2009 | Beyar et al. |
| 7,766,894 B2 | 8/2010 | Weitzner et al. |
| 8,142,458 B2 | 3/2012 | Shturman |
| 8,187,229 B2 | 5/2012 | Weitzner et al. |

(Continued)

*Primary Examiner* — Brian Szmal
(74) *Attorney, Agent, or Firm* — Blair Walker IP Services, LLC (57) ABSTRACT

A guidewire manipulation device includes a housing sized to be supported by a hand of a user, the housing having a distal end and a proximal end; a rotation member rotationally disposed within the housing; a locking assembly coupled to the rotation member, the locking assembly configured to selectively transfer rotational movement of the rotation member to rotational movement of a guidewire; a handle coupled to the housing and configured to be operable by the hand of the user; and a drive system coupled to the handle, the drive system configured to apply alternating clockwise motion and counter-clockwise motion to the guidewire by causing the rotation member to rotate.

20 Claims, 12 Drawing Sheets

(56) References Cited

U.S. PATENT DOCUMENTS

| | | |
|---|---|---|
| 2002/0177789 A1 | 11/2002 | Ferry et al. |
| 2003/0088187 A1 | 5/2003 | Saadat et al. |
| 2005/0240116 A1 | 10/2005 | Saadat et al. |
| 2005/0240120 A1 | 10/2005 | Modesitt |
| 2005/0277851 A1 | 12/2005 | Whittaker et al. |
| 2006/0041245 A1 | 2/2006 | Ferry et al. |
| 2006/0074442 A1 | 4/2006 | Noriega et al. |
| 2006/0282150 A1 | 12/2006 | Olson et al. |
| 2007/0016105 A1 | 1/2007 | Mamourian |
| 2007/0060879 A1 | 3/2007 | Weitzner et al. |
| 2007/0219467 A1 | 9/2007 | Clark et al. |
| 2007/0270755 A1 | 11/2007 | Von Oepen et al. |
| 2009/0082722 A1 | 3/2009 | Munger et al. |

GUIDEWIRE MANIPULATION DEVICE

INCORPORATION BY REFERENCE TO ANY PRIORITY APPLICATIONS

This application is a continuation of U.S. patent application Ser. No. 11/874,836, filed on Oct. 18, 2007, and is incorporated in its entirety by reference herein for all purposes, which claims the benefit of priority to U.S. Provisional App. No. 60/853,731, filed on Oct. 21, 2006, which is incorporated in its entirety by reference herein for all purposes. Priority is claimed pursuant to 35 U.S.C. §120 and 35 U.S.C. §119.

BACKGROUND OF THE INVENTION

The present invention generally relates to the maneuvering of a guidewire in surgical procedures where an 'endovascular' technique is employed to access vasculature of a patient. Additional background information can be found in U.S. Pat. No. 5,634,475, the contents of which are hereby incorporated by reference.

A guidewire is typically a semi-rigid probe used as an initial access point for performing am endovascular procedure. The guidewire is twisted, bent, and otherwise maneuvered through an access vessel in order to portion the guidewire tip at a location a surgeon would like to treat.

Convention guidewire manipulation methods often involve applying "torque" to the guidewire to aid its passage through tortuous and clogged vessels. This maneuver is performed by quickly and stiffly spinning the wire in one's fingertips. This torque helps curve or manipulate the guidewire through an obstruction or difficult passageway. This technique is also known as "helicoptering", alluding to the spinning blades of a helicopter.

However, applying torque remains difficult since guidewires are extremely thin in diameter and typically have a low friction surface. Additionally, the gloves of a surgeon are often coated with blood or saline solution, further increasing the slackness of the guidewire. In this respect, helicoptering and similar maneuvers can be time consuming and inefficient. This inefficiency not only frustrates surgeons but also increases procedure times and therefore procedure costs.

Present guidewires designs attempt to address these problems by providing a torque handle consisting of a plastic tube that is about 0.5 inches in diameter and three inches long that slips over the proximal end of the guidewire and looks in place. The surgeon manipulates this torque device (Olcott Torque Device) to facilitate rotational motion of the guidewire and grip.

These current techniques and practices have several problems. First, the current torque devices require a surgeon to concentrate on spinning the guidewire with the attached torque device. The spinning technique greatly depends on the ability of the user and can be difficult to learn. Thus, these devices remain inefficient and often highly dependent on the operator skill. Since it is highly desirably to place a guidewire quickly and therefore finish a procedure quickly, a more consistently controllable guidewire placement device that overcomes these disadvantages is desired.

OBJECTS AND SUMMARY OF THE INVENTION

It is therefore an object of the invention to provide a strong, non-slip grip on a guidewire.

It is another object of the invention to use a powered motor to spin a guidewire on a surgeon's command.

It is another object of the invention to spin the guidewire using a motorized guidewire spinning mechanism to provide optimal torque and technique that would thus be operator (i.e. surgeon) independent. For example, helicoptering with the spinning mechanism by rapidly twisting the guidewire about 180 degrees to the left and then rapidly spinning the guidewire to the right. In another example, rapidly spinning the guidewire in one direction.

It is another object of the invention to use a motorized mechanism to helicopter the guidewire in a number of different patterns dependant on the surgeon's need. Such patterns include, but are limited to a full clockwise rotation, a full counterclockwise rotation, continuous clockwise or counterclockwise rotations or any combination of the above.

It is another object of the invention to provide a vibration mechanism to allow the guidewire to vibrate to help the guidewire travel past a distal obstruction.

It is another object of the invention to utilize a roller mechanism to attain efficient traction on a guidewire. These rollers may be rubberized to provide traction in case the wire is slippery from liquids or due to a slick coating provided by the manufacturer.

It is another object of the invention to, via a roller system, allow for manual control of guide we spinning using a large cog-like manual control which would "torque" the guidewire using the surgeon's finger motion. Gears within the system may also be used to maximize the surgeon's finger motion efficiency. This manual control can be in addition to, or instead of, a motorized embodiment.

It is another object of the invention to use a lever-operated system to provide guidewire torque in an alternate embodiment with or without electric motor power. This system provides guidewire torque in a variety of patterns which mimics current surgical technique performed by hand.

In one preferred embodiment, the present invention is directed to a guidewire manipulation device for providing a user with guidewire manipulation techniques. Preferably, the guidewire manipulation device includes a lightweight housing (e.g., plastic) in which a powered motor drives a tandem roller assembly. The guidewire is passed through a hole positioned lengthwise through the device where the roller assembly engages the guidewire's outer surface.

The interface of the manipulation device includes a power button that directs the internal roller assembly to roll the guidewire in a desired rotational direction. Additional interface controls are also preferable to provide a different roll patterns, depending upon surgeon preference and guidewire placement efficiency.

In an alternate embodiment the roller assembly may be driven by a thumb wheel. Preferably, the roller assembly is spring-loaded, allowing the surgeon to roll the thumb control wheel in one direction and then have the guidewire automatically roll back in the opposite direction.

The manipulation device may be reusable or disposable and may delude contours to provide an ergonomic grip for the user.

DETAILED DESCRIPTION OF THE INVENTION

Figure 1:
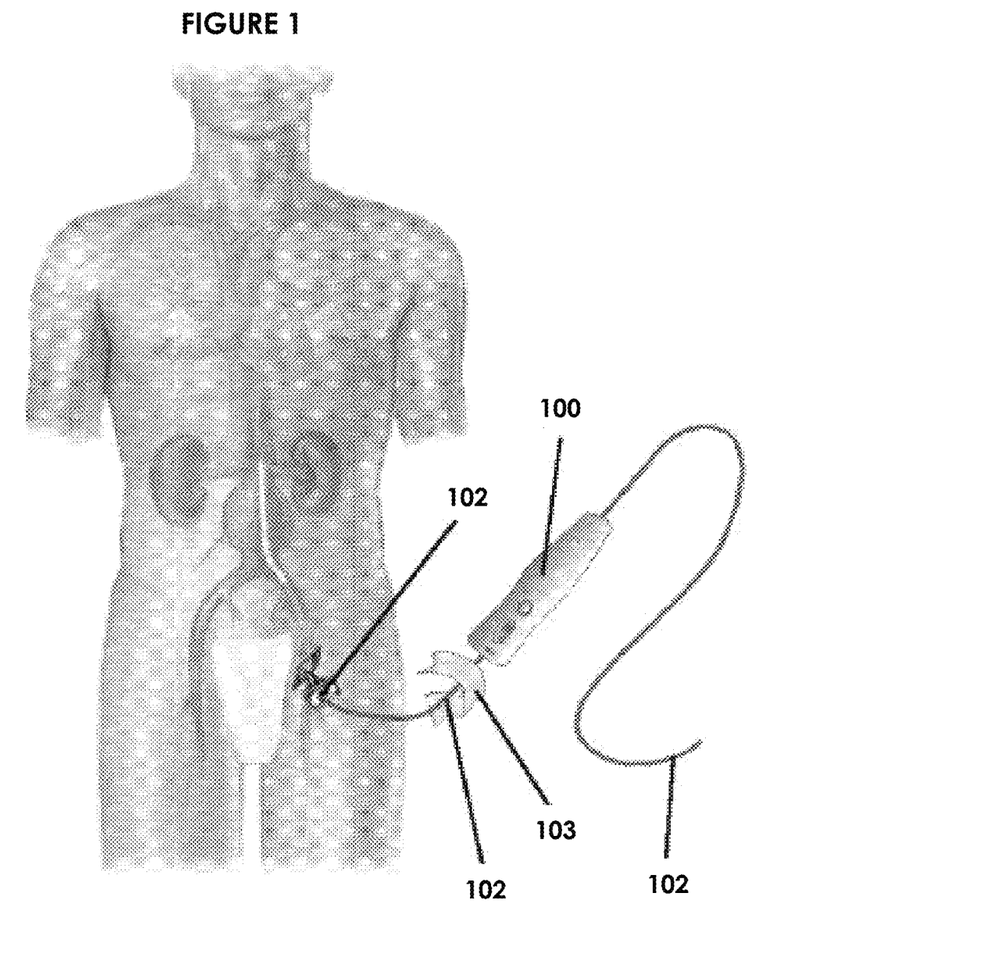
FIG. 1 illustrates a view of a guidewire manipulation device being used on a patient according to a preferred embodiment of the present invention.

FIG. 1 illustrates a preferred embodiment of a guidewire manipulation device 100 which is advanced over a guidewire 103. As seen in this figure, the guidewire 102 is introduced into the vessel of the patient (e.g., a femoral artery). The manipulation device 100 is slid over the guidewire 102 and selectively locked on to the guidewire 102. As the guidewire 102 is advance into the patient, the user operates the manipulation device 100 to rotate or vibrate the guidewire 102 as appropriate.

For example, as a distal end of the guidewire 102 reaches an angled or curved region of the vessel, the user activates the manipulation device 100 to rotate the guidewire 102 (i.e., in a counter clockwise direction indicated by arrow 103), thereby causing the distal end of the guidewire 102 to more easily advance through the angled or curved region. In another example, the distal end of the guidewire 102 reaches an obstruction (e.g., an embolism) but is unable to easily pass. The user then activates the guidewire manipulation device 102 to vibrate (e.g., by routing between a clockwise and counter clockwise direction quickly), thereby causing the distal end of the guidewire 12 to pass through the obstruction, in another example, the device 100 may include a multiple, preprogrammed rotation patterns appropriate for different vessel configurations (e.g., a 180 degree clockwise rotation followed by 180 degree counter clockwise rotation, a 90 degree clockwise rotation followed by 90 degree counter clockwise rotation or a 30 degree clockwise rotation followed by 180 degree counter clockwise rotation). The device may also include a microprocessor and memory connected to the motor and button 108 for storing and executing the preprogrammed rotation patterns.

Figure 2A:
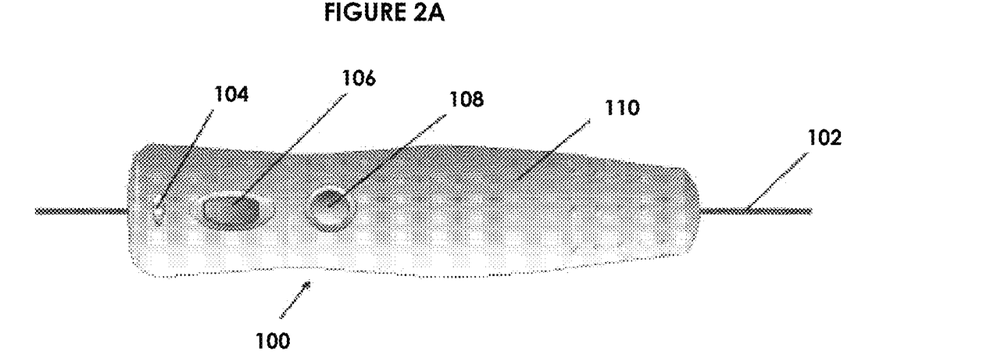
FIG. 2A illustrates a top view of the guidewire manipulation device of FIG. 1.
Figure 2B:
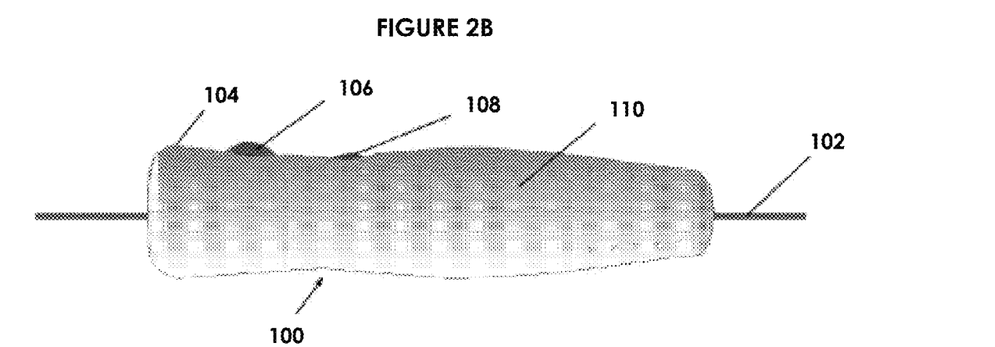
FIG. 2B illustrates a side view of the guidewire manipulation device of FIG. 1.

FIGS. 2A and 2B illustrate external views of the guidewire manipulation device 100. As seen in these figures, the guidewire 102 passes through a passage along the length of the device 100. Preferably, the manipulation device 100 includes a locking assembly in the form of a guidewire lock switch 106 which allows the user to selectively lock the device 100 to the guidewire 102. In this respect, the device 100 can move relative to the guidewire 102 in an unlocked state, and can move the guidewire 102 in a locked state.

The device 100 also preferably includes a power indicator light 104 (e.g., an LED) which indicates if the device 100 is powered on and a rotation button 108 which causes the guidewire 102 to rotate. Optionally, the device 100 may include a button, switch or similar mechanism to toggle the device 100 between rotating m a clockwise direction or a counter clockwise direction. Alternately, the button 108 may include multiple actuation techniques for determining clockwise or counter clockwise rotation (e.g., sliding forward or backward, multiple button presses, etc.).

Preferably, an outer container or casing 110 is composed of a light-weight material such as plastic and has an ergonomic shape that at least partially fits in the user's hand. In this respect, the user can comfortably operate the device 100 during a procedure.

Figure 3:
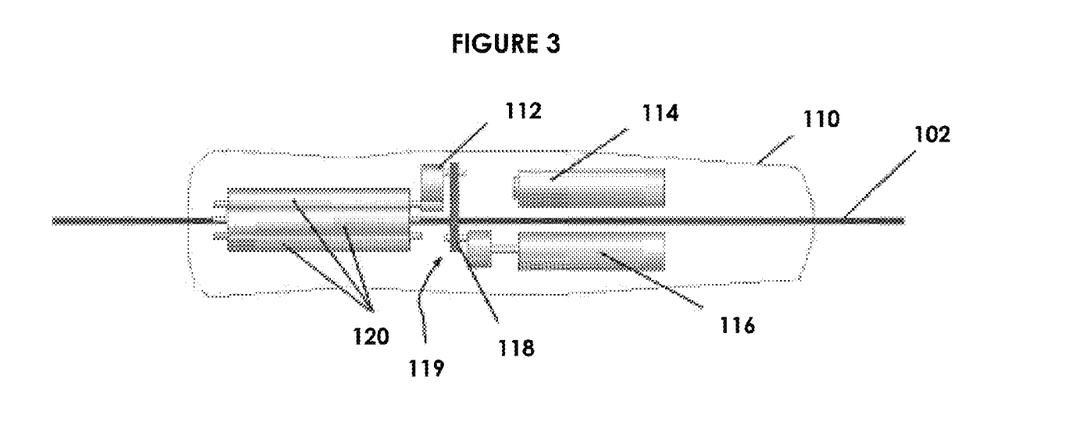
FIG. 3 frustrates a top open view of the guidewire manipulation device of FIG. 1.
Figure 4:
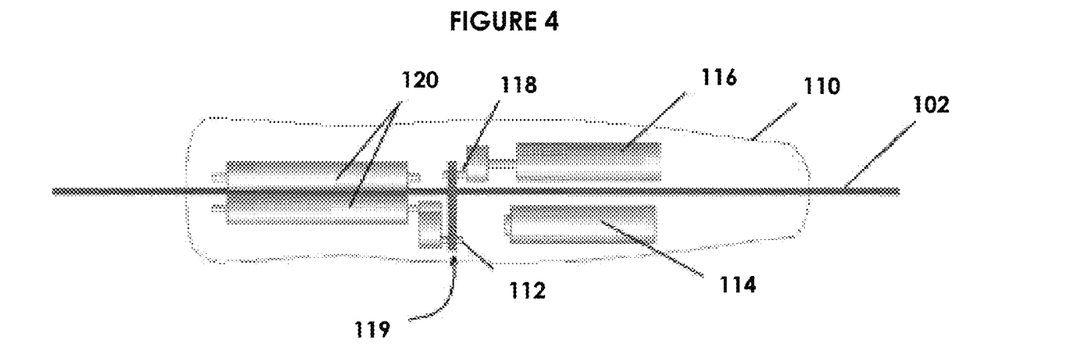
FIG. 4 illustrates a bottom open view of the guidewire manipulation device of FIG. 1.
Figure 5:
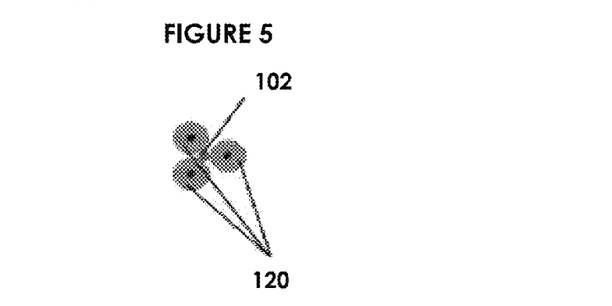
FIG. 5 illustrates a cross sectional view of the rollers of the guidewire manipulation device of FIG. 1.

Referring to FIGS. 3 and 4, an interior view of the device 100 within the outer easing 110 is illustrated according to a preferred embodiment of the present invention. The guidewire 102 is engaged by the device 100 with elongated rollers 120 (also seen in the cross sectional view of FIG. 5). Preferably the device 100 includes at least three rollers, however, any number of rollers 120 are possible (e.g., 1-5 rollers). When; the button 108 is pressed, the rollers 120 rotate, thereby rotating the guidewire 102. Preferably, the lock 108 raises or lowers one or more of the rollers 120 in relation to the guidewire 102, so as to lock the guidewire 102 with the device 100 when the rollers 120 are pressed against the guidewire 102 and unlock the guidewire 102 from the device 100 when the roller(s) 120 are moved away from the guidewire 102.

One or more of the rollers 120 are preferably driven by a motor 118 which is powered by battery 114 (or alternately by A.C. power such as an outlet). The motor 116 connects to the rollers 120 by a cam 119 made up of a first linkage 118 connected to the motor 116 and a second linkage 112 connected to the roller 120. In this respect, activation of the motor 116 drives the cam 110 and ultimately rotation of the roller 120.

Figure 6:
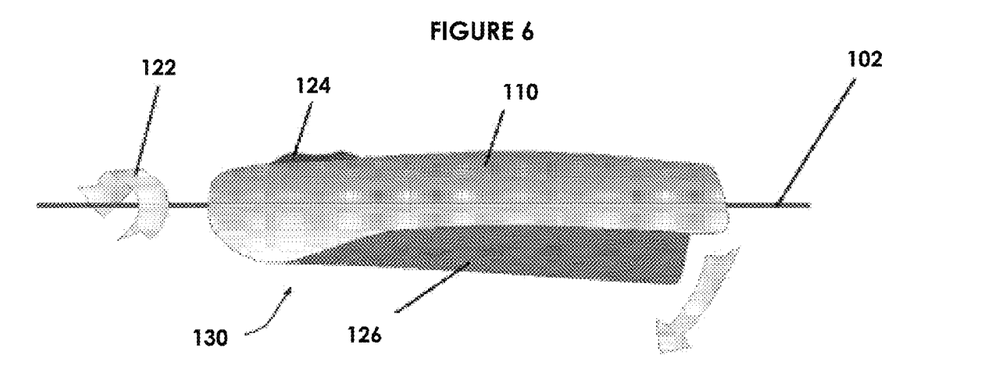
FIG. 6 illustrates a side view of a guidewire manipulation device according to a preferred embodiment of the present invention.
Figure 7:
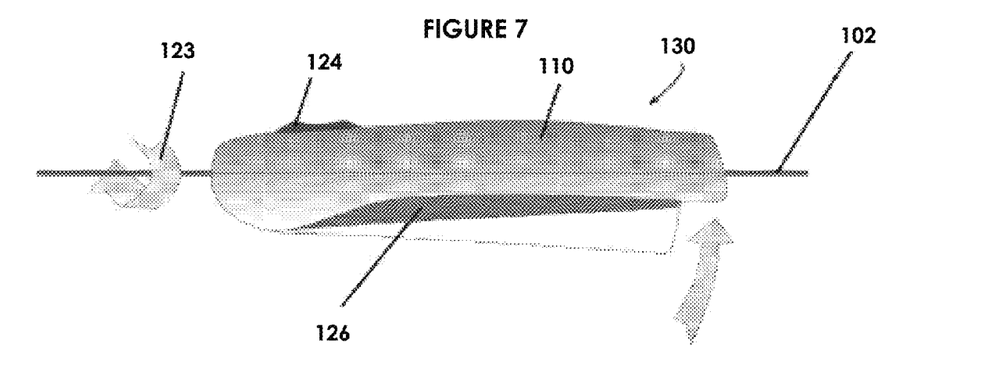
FIG. 7 illustrates a side view of the guidewire manipulation device of FIG. 6 with a depressed trigger according to a preferred embodiment of the present invention.

FIGS. 6 and 7 illustrate another preferred embodiment of a manual manipulation device 130 according to the present invention. The device 130 is generally similar to the previously described device 100, except that the rollers 120 and therefore rotation at the guidewire 102 is driven by a handle 126. For example, depressing the handle 126 rotates the guidewire 102 in a clockwise direction (arrow 122) and releasing the handle 126 rotates the guidewire 102 in a counter clockwise direction (arrow 124). Additionally, switch 124 is included to change a type of rotation caused by the handle 126. For example, the switch 124 may change a gear ratio and therefore the amount of rotation cause by depressing the handle. In another example, the switch 124 may change directions of rotation caused by depressing the handle 126.

Figure 8:
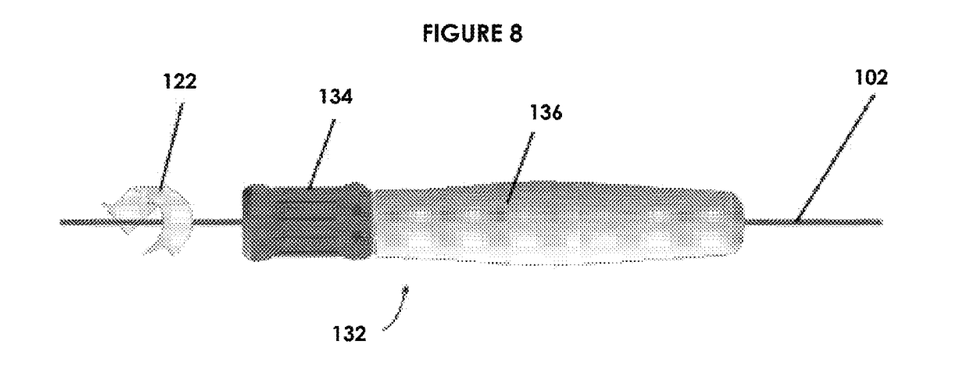
FIG. 8 illustrates a side view of a guidewire manipulation device according to a preferred embodiment of the present invention.
Figure 9:
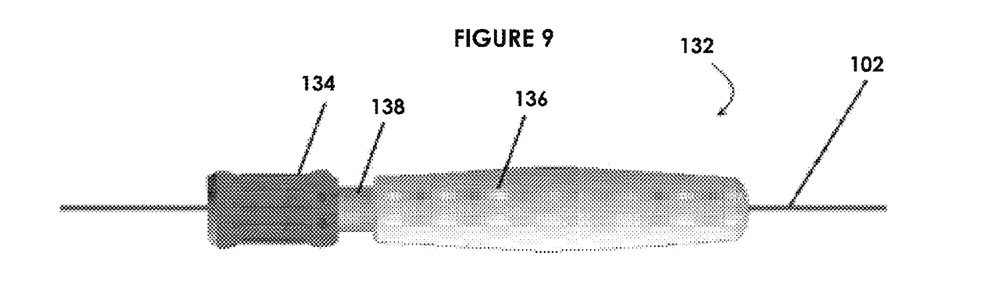
FIG. 9 illustrates a side view of the guide-wire manipulation device of FIG. 8.
Figure 10:
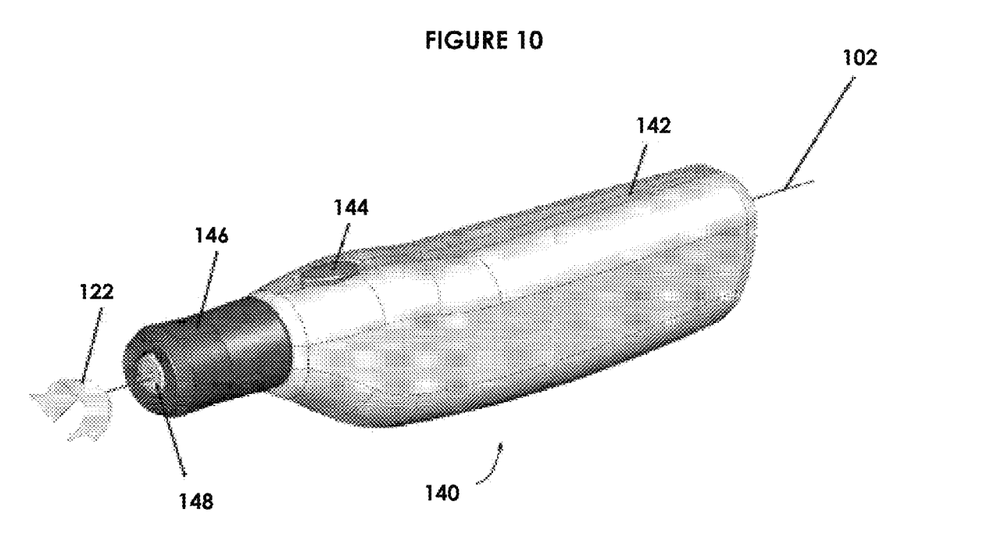
FIG. 10 illustrates a perspective view of a guide-wire manipulation device according to a preferred embodiment of the present invention.

FIGS. 8 and 9 illustrate another preferred embodiment of a manual guidewire manipulation device 132 which is generally similar to the previously described devices 100 and 130. However, the device 132 includes a selectively locking thumb roller 133 on a distal end of the device 132. The thumb roller 132 includes a locked mode, seen in FIG. 8, in which the roller 134 is engaged with the guidewire 102, thereby allowing the user to roll the roller 134 and thus the guidewire 102. The thumb roller 132 also includes an unlocked mode, seen in FIG. 9, in which the roller 134 is pulled distally from the casing 136, exposing space 138 and disengaging the relief 134 from the guidewire 102. Thus, in the unlocked mode, the device 132 can be moved along the length of the guidewire 102.

Figure 11:
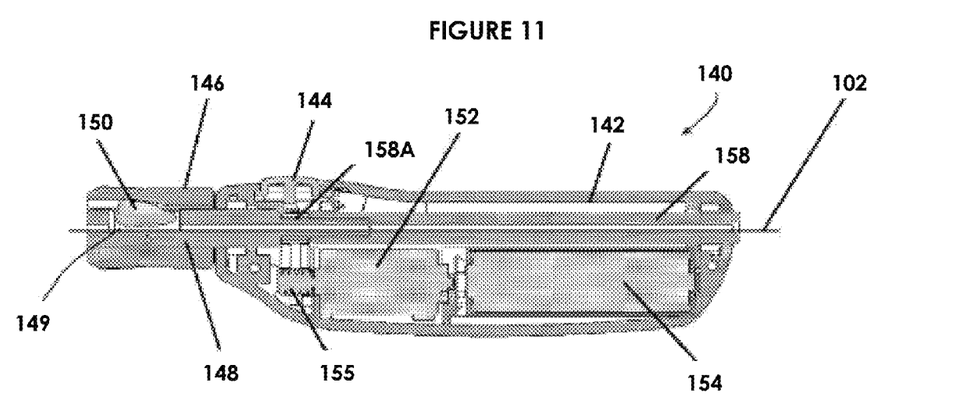
FIG. 11 illustrates a side cross sectional view of the guidewire manipulation device of FIG. 10.
Figure 12:
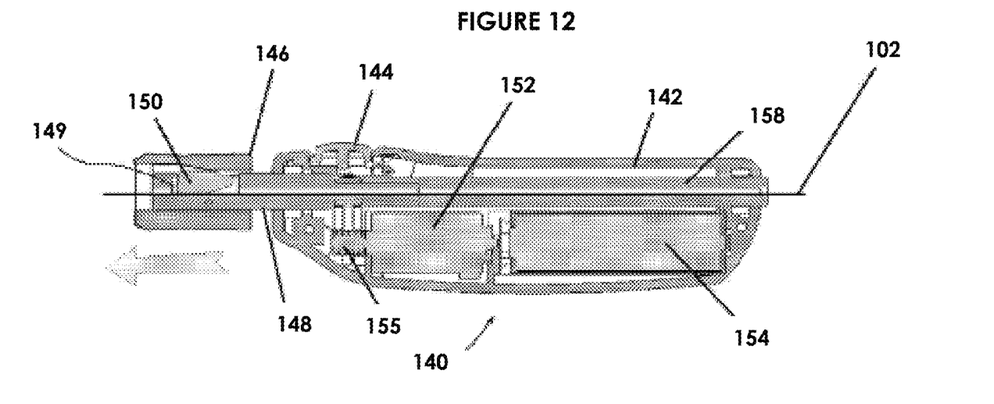
FIG. 12 illustrates a side cross sectional view of the guidewire manipulation device of FIG. 10.
Figure 13:
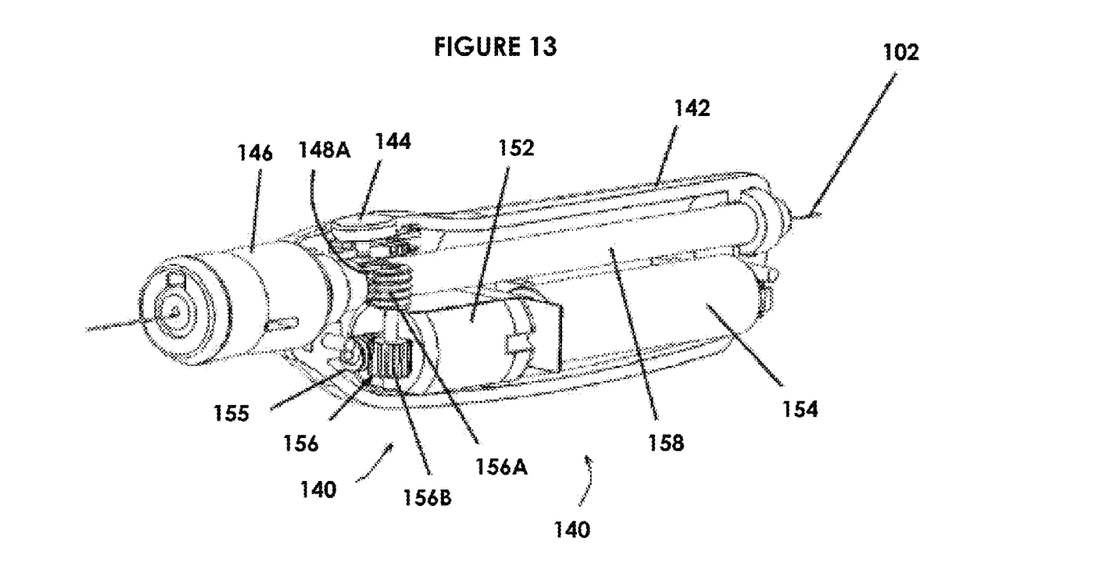
FIG. 13 illustrates a perspective open view of the guidewire manipulation device of FIG. 10.
Figure 14:
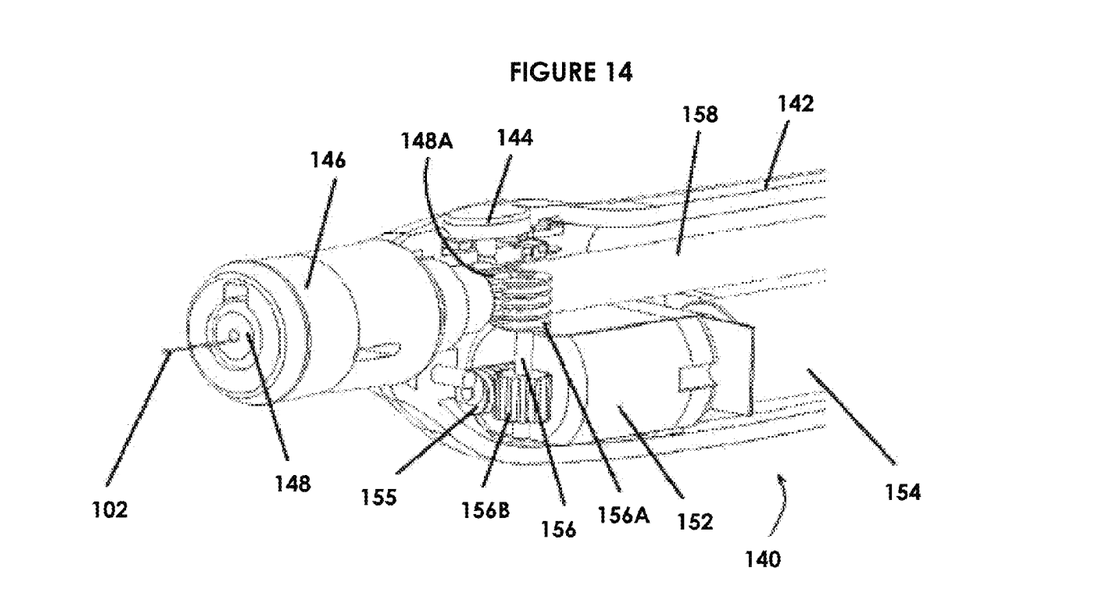
FIG. 14 illustrates a perspective open view of the guidewire manipulation device of FIG. 10.
Figure 15:
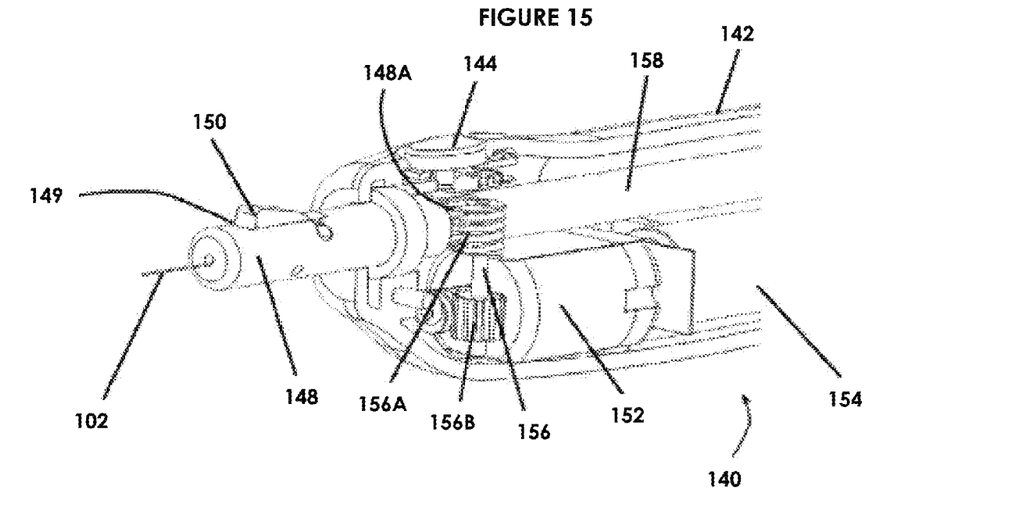
FIG. 15 illustrates a perspective open view of the guidewire manipulation device of FIG. 10.

FIGS. 10-15 illustrate another preferred embodiment of a guidewire manipulation device 140 according to a preferred embodiment of the present invention. The device 140 is generally similar to the previously described device 100. For example, the device 140 includes a hand-held (e.g., steed to be held within a users hand), ergonomic, outer case 142 and a manipulation button 144. As best seen in FIGS. 11 and 12, the device 140 also includes a motor 152 powered by a battery 154 and a guidewire passage 158.

Preferably, the device 140 includes a locking assembly in the form of a locking hub 146 (similar to the device 132) which allows the user to selectively lock the guidewire 102 with the device 140. The locking hub 146 allows free movement of the guidewire 102 when positioned near the case 142 (FIG. 17) and locks the guidewire 102 when the hub is pulled away from the case 142 (FIG. 12). The hub 146 includes an interior cavity with a top surface angled downward towards the case 142. Within the interior cavity is a locking wedge 150 which is located within a window 149 of a tube 148 that exposes the guidewire 102. In the unlocked position of FIG. 11, the hub 146 restrains the wedge 150 but does not press down on the wedge 150, thereby allowing the guidewire 102 to slide underneath the wedge 150. In the locked position of FIG. 12, the angled interior surface of the hub 146 forces the wedge downward against the guidewire 102, preventing the guidewire from movement relative to the device 140. A perspective view of the wedge 150 can also be seen in FIG. 15.

As seen in FIGS. 11-15, the motor 152 includes a worm gear 155 that engages a first gear section 156B of shaft 156. A second gear section 158A of shaft 158 engages gearing 158A on the outer surface of tube 148. In this respect, when the motor 152 is activated, it ultimately rotates the roller assembly, or tube 148. Thus, the hub 148 must be in a slid-out, locked position to cause the guidewire 102 to rotate.

As with all motorized embodiments described in this specification, the device 140 may also include a microprocessor and memory for storing and executing different rotation sequences (i.e., rotation directions and rotation speeds).

Figure 16:
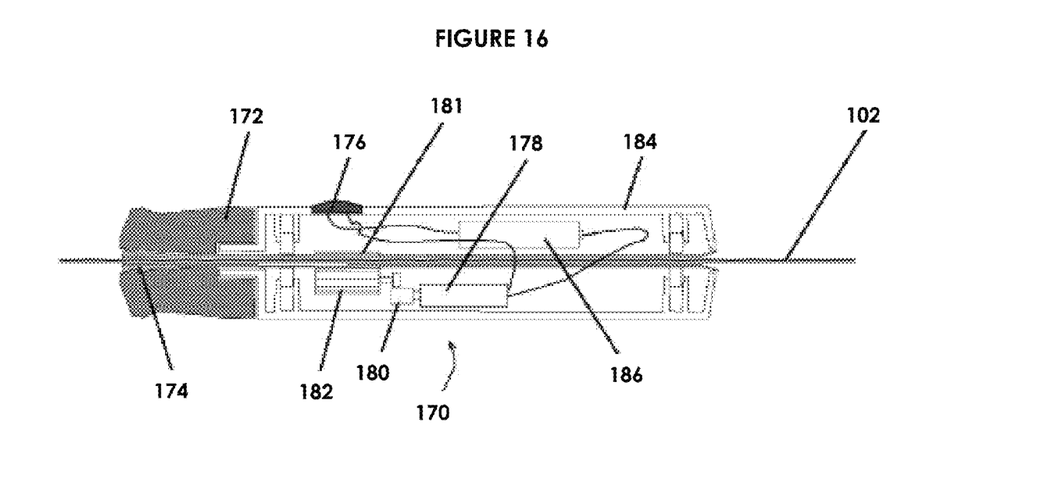
FIG. 16 illustrates a side open view of a guidewire manipulation device according to a preferred embodiment of the present invention.
Figure 17:
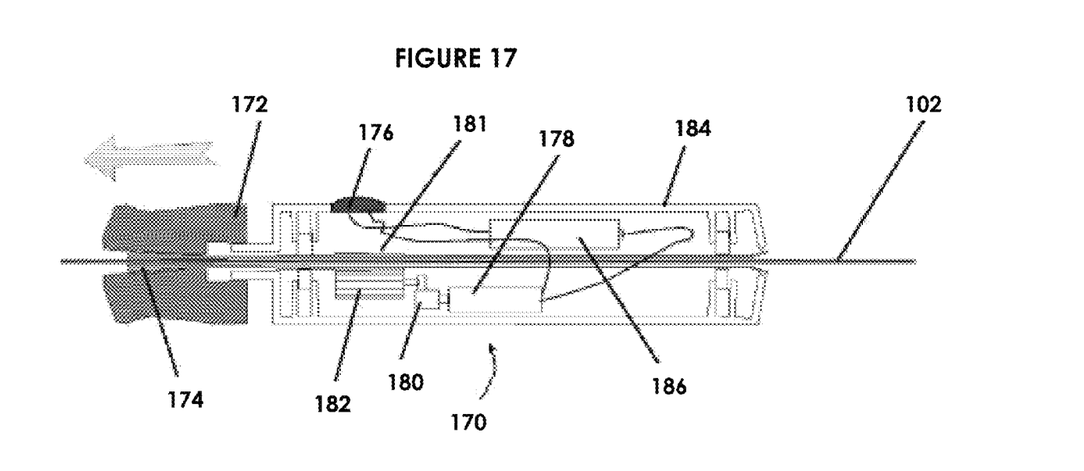
FIG. 17 illustrates a side open view of the guidewire manipulation device of FIG. 16.

FIGS. 16 and 17 illustrate a guidewire manipulation device 170 according to yet another preferred embodiment according to the present invention. The device 170 is generally similar to previously described embodiments, including an outer case 184 having an actuation button 176 that is coupled to a battery 186 and a motor 178. The gear 180 of the motor 178 is engaged with a gear 182 that is also engaged with a geared section 181 on wedge tube 174.

A hub 174 includes an interior, angled passage that increases in diameter in a distal direction. The wedge tube 174 is partially positioned within the hub 174. In the unlocked position of FIG. 16, the angled passage of the hub 172 complements a distally expanding shape of the wedge tube 174, thereby preventing the wedge tube 172 from clamping or providing fore(c) on the guidewire 102 and thus allowing the guidewire 102 to slide and rotate relative to the device 170. In the looked position of FIG. 17, the hub 172 is moved distally from the case 184, causing the smaller diameter of the interior passage of the hub 172 to wedge or clamp on to the expanded distal end of the wedge tube 174. Thus, the wedge lobe 174 (preferably composed of a compressible, semi-compressible or deformable material) closes around the guidewire 102, maintaining the position of the guidewire 102 relative to the device 170 and further allowing rotation of the guidewire 102.

Figure 18:
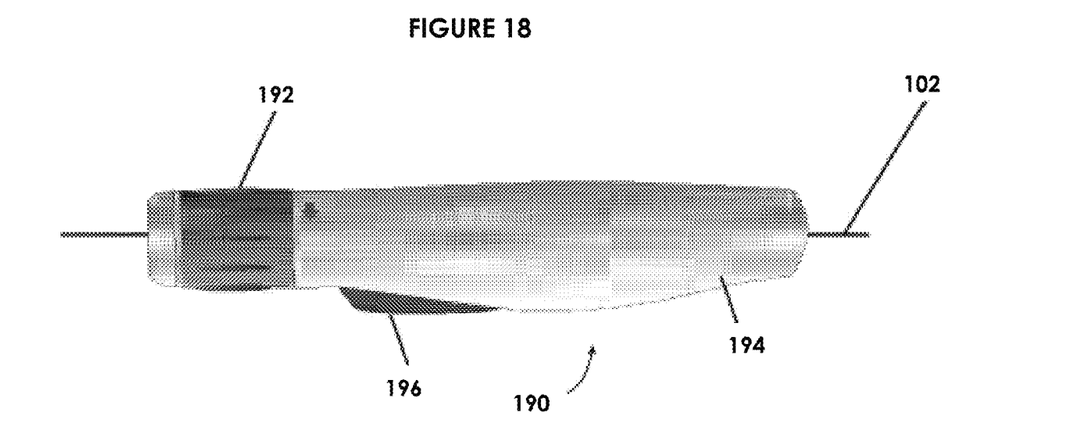
FIG. 18 illustrates a side view of a guidewire manipulation device according to a preferred embodiment of the present invention.

FIG. 18 illustrates another preferred embodiment of a device 190 according to the present invention. The device 190 is generally similar to the previously described devices. However, the device 190 includes a looking assembly in the form of a guidewire lock activated by depressing a trigger 196. In this respect, the user can rotate hub 192, either clockwise or counter clockwise to respectively rotate the guidewire 102.

Figure 20:
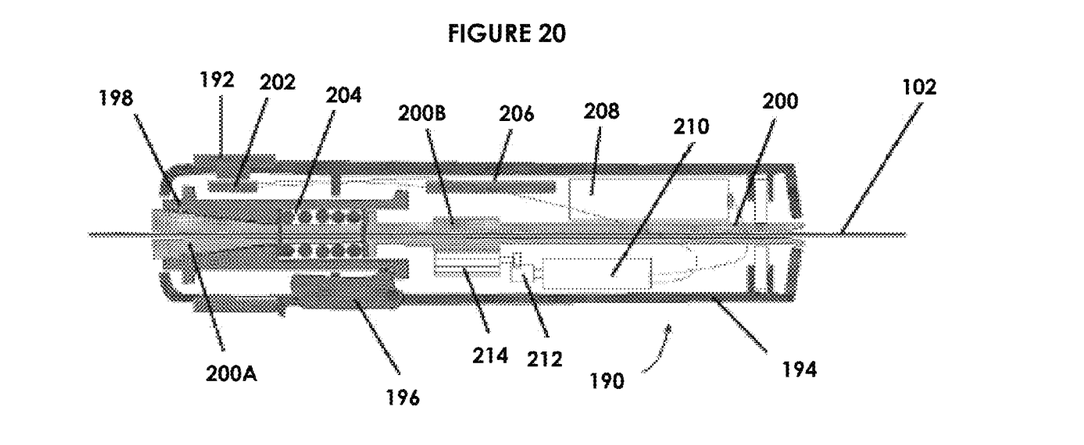
FIG. 20 illustrates a side open view of the guidewire manipulation device of FIG. 19.

FIGS. 18 and 20 illustrate another preferred embodiment of a guidewire manipulation device 190 according to the present invention. The device 190 is generally similar to the previously described embodiments, including a motor 210 powered by a battery, a gear 214 coupled to an output gear 212 of the motor 210 and to a geared portion 200B of a wedge tube 200 and a case 194 to contain the components. The motor 210 is controlled by a rocker switch 192 that is connected to a first circuit board 202 which sends the position of the rocker switch 192 to the second circuit board 206. The second circuit board 206 includes a microprocessor and memory for executing a plurality of rotation programs. These rotation programs direct the motor 210 to make predetermined rotation movements such as in a single direction, exponentially Increasing rotational speed, quick rotation to cause vibration or a predetermined series of rotational movements. Thus, more complicated movements can be performed by the user.

The device 190 locks on to the guidewire 102 when the user releases trigger 196 (see FIG. 19) and unlocks the guidewire 102 when the user depresses trigger 196. The trigger 196 moves an outer tubing 198 which is biased in a distal direction by a spring 204. The interior passage of the outer tubing 138 increases in diameter in a distal direction forming an inverted cone shape. An inner wedge tube 200 is positioned within the passage of the outer tubing 198 and includes a wedge 200A that increases in size in a distal direction of the device 190. The guidewire 102 is located within a passage of the wedge tube 200.

Figure 19:
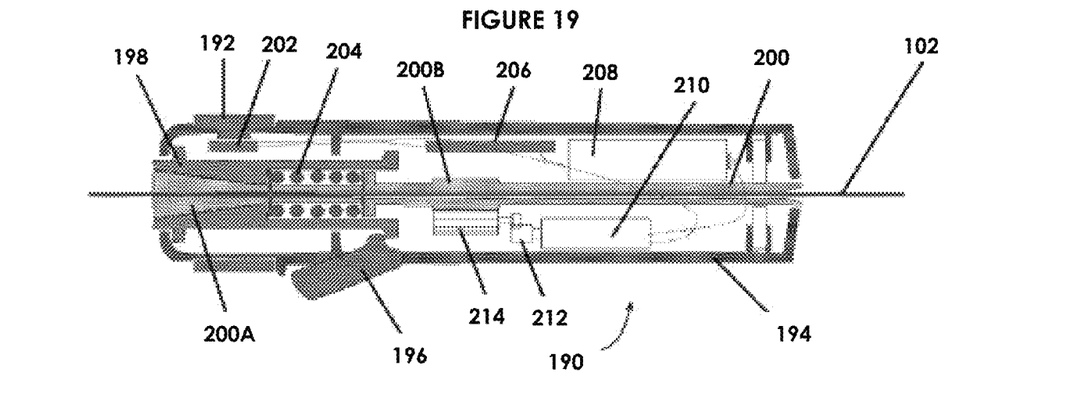
FIG. 19 illustrates a side open view of a guidewire manipulation device according to a preferred embodiment of the present invention.

When the trigger 196 is released, as in FIG. 19, the outer tubing 198 is moved distally by the spring 204, causing the smaller diameter region of the inner passage of the outer tubing 198 to press against the wedge 200A of wedge tube 200. The wedge 200 then compresses around the guidewire 102, locking the guidewire 102 in place relative to the device 190. When the trigger 196 is depressed, a portion of the trigger 136 pushes the outer tubing 198 in a proximal direction, against the bias of the spring 204. The angled portions of the inner passage of the outer tubing 198 move away from the wedge 200a, allowing the inner passage of the wedge tube 200 to release the guidewire 102. Thus, the user can selectively lock on to and rotate the guidewire 102 (with the roller assembly, including wedge tube 200) by releasing the trigger 196 and pressing the actuation button 192.

Figure 21:
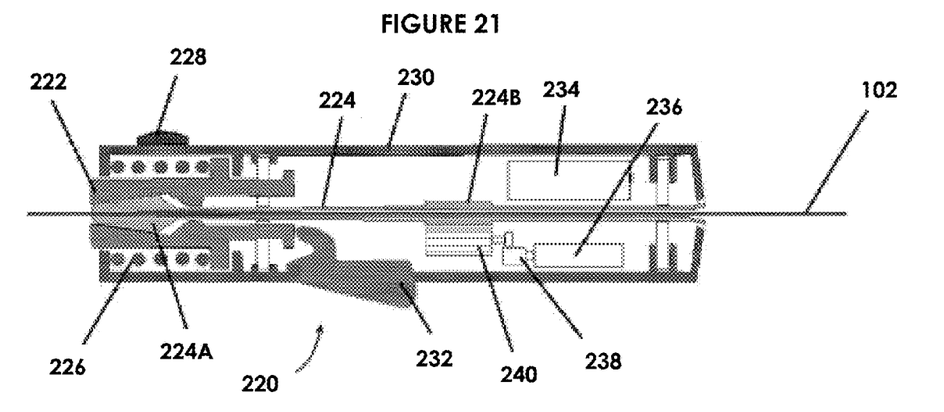
FIG. 21 illustrates a side open view of a guidewire manipulation device according to a preferred embodiment of the present invention.
Figure 22:
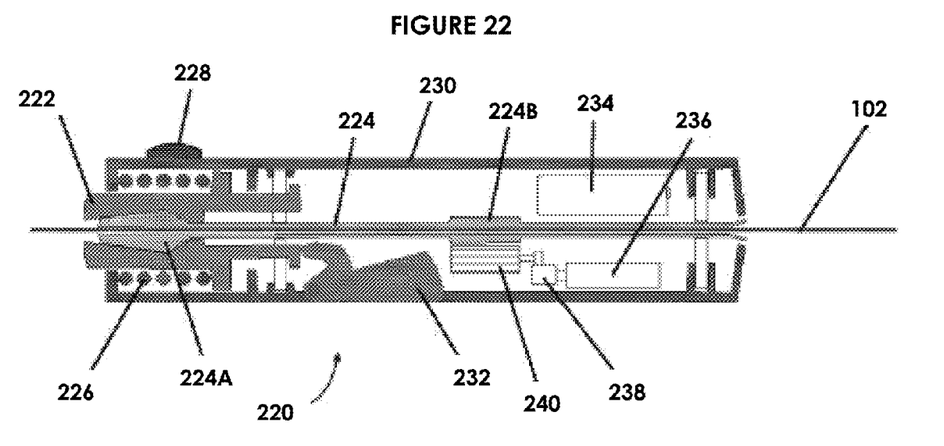
FIG. 22 illustrates a side open view of the guidewire manipulation device of FIG. 21.

FIGS. 21 and 22 illustrate another preferred embodiment of a guidewire manipulation device 220 according to the present invention. The device 220 is generally similar to the previously described embodiments. Including a battery 234 powering a motor 236 which drives a wedge tube 224 (via a gear 240 connected to geared region 224B and output gear 238) and an actuation button 220.

The device 220 further includes a locking mechanism assembly that locks the lateral position of the guidewire 102. As seen in FIG. 21, when the user releases the trigger 232, the device remains in a locked position, allowing the user to rotate the guidewire 102. As seen in FIG. 22, when the user depresses the trigger 232, the device remains in an unlocked position, allowing the user to slide the device 220 along the guidewire 102 and preventing guidewire rotation.

In the locked position, the trigger 232 maintains an outer tube 222 in a proximal position, proximally biased by a spring 226. The outer tube includes an inner passage that generally decreases in diameter in a distal direction. The inner surface of the outer tube 222 presses against a wedge portion 224A of a wedge tube 224, causing the wedge tube 224 to press against and lock onto the guidewire 102.

In the unlocked position, the trigger 232 pushes the outer tube 222 distally, against the bias of the spring 226. The surface of the inner passage of the outer tube 222 moves away from the wedge 224A, releasing the wedge tube 224 from the guidewire 102.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A guidewire manipulation device comprising:
a housing sized to be supported by a hand of a user, the housing having a distal end and a proximal end;
a rotation member rotationally disposed within the housing;
a locking assembly coupled to the rotation member, the locking assembly configured to selectively transfer rotational movement of the rotation member to rotational movement of a guidewire;
a handle coupled to the housing and configured to be operable by the hand of the user; and
a drive system coupled to the handle, the drive system configured to apply alternating clockwise motion and counter-clockwise motion to the guidewire by causing the rotation member to rotate.

2. The guidewire manipulation device of claim 1, wherein the handle is configured to be depressed by the user such that the handle moves in a first direction in relation to the housing.

3. The guidewire manipulation device of claim 2, wherein the handle is configured to cause rotation of the rotation member in a first rotational direction when the handle is moved in the first direction in relation to the housing.

4. The guidewire manipulation device of claim 3, wherein the handle is configured to be releasable by the user such that the handle is moved in a second direction in relation to the housing, the second direction different from the first direction.

5. The guidewire manipulation device of claim 4, wherein the handle is configured to cause rotation of the rotation member in a second rotational direction, opposite the first rotational direction, when the handle is moved in the second direction in relation to the housing.

6. The guidewire manipulation device of claim 2, further comprising a switch configured to select a direction of rotation that the rotation member rotates when the handle is depressed by the user.

7. The guidewire manipulation device of claim 1, further comprising an ergonomic shape associated with the housing for providing a grip surface for the hand of the user.

8. The guidewire manipulation device of claim 1, wherein the locking assembly has a locked mode wherein the rotation member is engaged with the guidewire, and an unlocked mode wherein the rotation member is disengaged from the guidewire.

9. The guidewire manipulation device of claim 8, wherein the locking assembly includes a manual interface configured to move the locking assembly between the locked mode and the unlocked mode.

10. The guidewire manipulation device of claim 9, wherein the manual interface is disposed at the distal end of the housing.

11. The guidewire manipulation device of claim 9, wherein the manual interface is configured to receive rotational input from the user.

12. The guidewire manipulation device of claim 1, wherein the drive system is configured to cause the rotation member to rotate such that at least 90 degrees of rotation is applied to the guidewire in a clockwise direction and at least 90 degrees of rotation is applied to the guidewire in a counter-clockwise direction.

13. A method for manipulating a guidewire, comprising:
providing a guidewire manipulation device comprising:
a housing sized to be supported by a hand of a user, the housing having a distal end and a proximal end;
a rotation member rotationally disposed within the housing;
a locking assembly coupled to the rotation member, the locking assembly configured to selectively transfer rotational movement of the rotation member to rotational movement of a guidewire;
a handle coupled to the housing and configured to be operable by the hand of the user; and
a drive system coupled to the handle, the drive system configured to apply alternating clockwise motion and counter-clockwise motion to the guidewire by causing the rotation member to rotate;
introducing a guidewire into a patient;
sliding the guidewire manipulation device over the guidewire;
engaging the rotation member with the guidewire;
actuating the manipulation device to rotate the guidewire in a first rotational direction.

14. The method of claim 13, wherein the step of actuating the guidewire manipulation device comprises holding the guidewire manipulation device in the hand of the user and operating the handle with the hand of the user.

15. The method of claim 13, wherein the step of actuating the guidewire manipulation device to rotate the guidewire in a first direction comprises manually moving the handle of the guidewire manipulation device.

16. The method of claim 13, wherein the step of actuating the guidewire manipulating device to rotate the guidewire in a first direction comprises depressing the handle of the guidewire manipulation device.

17. The method of claim 16, further comprising the step of actuating the manipulation device to rotate the guidewire in a second rotational direction, opposite the first rotational direction.

18. The method of claim 17, wherein the step of actuating the guidewire manipulating device to rotate the guidewire in a second direction comprises releasing the handle of the guidewire manipulation device.

19. The method of claim 13, wherein the step of engaging the rotation member with the guidewire comprises selectively transferring rotational movement of the rotation member to rotational movement of a guidewire by placing the locking assembly into a locked mode.

20. The method of claim 13, wherein the step of introducing the guidewire into a patient comprises introducing the guidewire into the vasculature of the patient.

\* \* \* \* \*